US006451345B1

(12) United States Patent
Percel et al.

(10) Patent No.: US 6,451,345 B1
(45) Date of Patent: Sep. 17, 2002

(54) FUNCTIONAL COATING OF LINEZOLID MICROCAPSULES FOR TASTE-MASKING AND ASSOCIATED FORMULATION FOR ORAL ADMINISTRATION

(75) Inventors: Phillip J. Percel, Troy; Krishna S. Vishnupad; Gopi M. Venkatesh, both of Dayton, all of OH (US)

(73) Assignee: Eurand Pharmaceuticals Ltd. (IE)

( * ) Notice: Subject to any disclaimer, the term of this patent is extended or adjusted under 35 U.S.C. 154(b) by 0 days.

(21) Appl. No.: 09/506,051

(22) Filed: Feb. 17, 2000

Related U.S. Application Data

(60) Provisional application No. 60/177,233, filed on Jan. 20, 2000.

(51) Int. Cl.[7] .............................. A61K 9/36; A61K 9/14; A61K 9/22; A61K 9/26; A61K 9/16
(52) U.S. Cl. ...................... 424/480; 424/468; 424/469; 424/489; 424/490; 424/493; 424/494; 424/495; 424/497; 424/501
(58) Field of Search ................................. 424/480, 464, 424/78.1, 468, 469, 489, 501, 497, 495, 493, 494, 490

(56) References Cited

U.S. PATENT DOCUMENTS

| | | | |
|---|---|---|---|
| 5,075,114 A | | 12/1991 | Roche |
| 5,082,669 A | | 1/1992 | Shirai et al. |
| 5,084,278 A | * | 1/1992 | Mehta ........................ 424/441 |
| 5,464,612 A | * | 11/1995 | Matoba et al. ............. 424/78.1 |
| 5,840,332 A | * | 11/1998 | Lerner et al. ................ 424/464 |
| 5,900,252 A | | 5/1999 | Calanchi et al. |

FOREIGN PATENT DOCUMENTS

| | | |
|---|---|---|
| EP | 0352781 | 1/1990 |
| WO | WO 88/03795 | 6/1988 |
| WO | WO 99/25344 | 5/1999 |
| WO | WO 99/37630 | 7/1999 |

OTHER PUBLICATIONS

International Search Report issued Jul. 26, 2001, by the International Searching Authority regarding corresponding PCT International Application No. PCT/US01/01414.
"Xyvox is the First in a New Class of Antibiotics," *Drug Infoline* web site, vol. 1, No. 1 (5/99).
"Using the newer antibiotics wisely; antibiotics such as quinolene or macrolide," *Medical Economics Company, Inc. Patient Care*. Sec. No. 14, vol. 33, p. 97, (Sep. 1999).

* cited by examiner

*Primary Examiner*—Thurman K. Page
*Assistant Examiner*—Blessing Fubara
(74) *Attorney, Agent, or Firm*—Thompson Hine LLP

(57) ABSTRACT

The present invention provides taste-masked microcapsules of Linezolid or the like (any member of the orally effective oxazolidinone or macrolide antibiotics), suitable for oral administration as a suspension, a fast-disintegrating, effervescent or chewable tablet, and more specifically relates to such oral dosage forms in which the bitter taste of Linezolid contained therein is masked by a combination of microencapsulation by solvent coacervation and subsequent functional membrane coating on said microcapsules. The taste-masked granules thus obtained release less than 5%, most preferably less than 3%, at a pH of 4.0 to 6.0 (pH of the saliva) but rapidly release (as a burst) at pHs of the upper intestinal tract. The taste-masked granules are optionally blended with other pharmaceutically acceptable excipients and filled into unit dose containers or compressed into fast-disintegrating/effervescent/chewable tablets. The contents of the Linezolid unit dose containers are suspended in an aqueous medium prior to oral administration to pediatric and geriatric patients, who are unwilling and/or find it difficult to swallow Linezolid tablets. In contrast, fast-disintegrating tablets on administration without water rapidly disperse into taste masked granules in the mouth.

21 Claims, No Drawings

US 6,451,345 B1

FUNCTIONAL COATING OF LINEZOLID MICROCAPSULES FOR TASTE-MASKING AND ASSOCIATED FORMULATION FOR ORAL ADMINISTRATION

CROSS REFERENCE TO RELATED APPLICATIONS

This application claims priority from U.S. Provisional Application No. 60/177,233 filed Jan. 20, 2000.

TECHNICAL FIELD

The present invention relates to effective taste masking while achieving rapid release of Linezolid as a burst in the upper intestinal tract using a combination of microencapsulation and functional coating.

More particularly, it relates to taste masked antibiotic particles which are composed of 1) a primary ethylcellulose coating of Linezolid needle-like crystals with a median particle size of 20 microns by solvent coacervation (producing Microcaps ®Linezolid), 2) an optional seal coat of shellac, and 3) an enteric coating.

BACKGROUND

Linezolid is one of the oxazolidinone antibiotics with a chemical name (S)-N-{{3-fluors4-(4-morpholinyl)phenyl}-2-oxo-5-oxazolidinyl)methyl}-acetimide; it is orally effective and fairly soluble in water. It is believed to be effective against bacteria resistant to other antibiotics. The present invention is directed to effective taste-masking of oxazolidinone antibiotics as well as other broad spectrum antibiotics such as macrolides.

A number of processes are widely used for masking the unpleasant, often bitter, taste of pharmacologically effective candidates. An overview by Roy, "Taste masking in oral pharmaceuticals", *Pharmaceutical Technology*, April 1994, pages 84–99 addresses a number of processes and formulations for achieving taste masking of bitter drugs. The techniques described herein and other documents such as U.S. Pat. No. 5,075,114 assigned to Roche, U.S. Pat. No. 5,082,669 to Shirai et al. and U.S. Pat. No. 5,084,278 to Mehta, use polymeric materials (single or in combination), such as cellulosic polymers and Eudragit L and E type.

SUMMARY OF THE INVENTION

In accordance with the present invention, taste masked granules of Linezolid, or other oxazolidinone or macrolide antibiotics, are obtained by a combination of microencapsulation (i.e., by coacervation of ethylcellulose in cyclohexane) and application of functional coating on said microcapsules, the latter including an optional seal coat and an enteric coat. By providing uniform, impervious high coating levels on bitter Linezolid crystals, the present invention not only provides extremely effective taste masking, but also rapid release of the drug in the upper intestine. While the discussion which follows references the use of Linezolid, it will be apparent that it also pertains to other orally effective oxazolidinone or macrolide antibiotics.

The taste-masked granules obtained as described above are optionally blended with other pharmaceutically acceptable excipients such as flavors, sweeteners, suspending agents and/or preservatives and filled into unit dose containers or compressed into fast disintegrating, effervescent or chewable tablets. Stable aqueous suspensions can be constituted from the contents of unit doses for oral administration up to 21 days of pediatric and geriatric patients who are unwilling and/or find it difficult to swallow tablets. Fast disintegrating tablets rapidly disintegrate in the mouth and are therefore suitable for oral administration to patients who find it difficult to swallow tablets. Such dosage forms on oral administration should release not more than 5%, most preferably not more than 3%, at pHs of the saliva but rapidly release at least 70% within an hour or so at pHs of the upper intestinal tract.

DETAILED DESCRIPTION

The present invention provides taste-masked microcapsules of Linezolid or the like (any member of the orally effective oxazolidinone or macrolide antibiotics), suitable for oral administration as a suspension, a fast-disintegrating, effervescent or chewable tablet, and more specifically relates to such oral dosage forms in which the bitter taste of Linezolid contained therein is masked by a combination of microencapsulation by solvent coacervation and subsequent functional membrane coating on said microcapsules. A taste-masked microcapsule composition for taste masking an orally effective oxazolidinone or macrolide antibiotic in accordance with the present invention comprises microcapsules of the drug in a polymeric coating matrix prepared by solvent coacervation of a microencapsulation polymer. The resulting microcapsules may be provided with an optional seal coat and then are coated with a plasticized enteric polymer. In the resulting taste masked microcapsule composition the coating materials account for approximately 30 to 60% of the composition by weight. The taste-masked granules thus obtained release less than 5%, more preferably less than 3%, at a pH of 4.0 to 6.0 (pH of the saliva) but rapidly release (as a burst) at pHs of the upper intestinal tract. Accordingly, the Linezolid or other orally effective oxazolidinone or macrolide antibiotic can be orally administered without producing an unpleasant taste of the drug because of the minimal release at the pH of the saliva and yet the drug is rapidly released in the upper intestinal tract.

In one embodiment of the invention, Linezolid crystals are microencapsulated by suspending in ethylcellulose solution in cyclohexane at 80° C. and cooling gradually. The process for the preparation of individual taste masked bitter tasting pharmaceuticals by microencapsulation of the pharmaceutical in a coacervation medium containing cyclohexane, an encapsulating polymer and a phase inducing agent is well known in the art. A typical process is described in U.S. Pat. No. 3,860,733 to Lewis D. Morse et al which discloses microencapsulation of vitamin mixes by polymer/polymer incompatibility coacervation. A disclosed coating polymer is ethylcellulose, a disclosed phase inducing polymer is polyethylene and a disclosed solvent for the polymers is cyclohexane. Because of its detailed description of the coacervation process, U.S. Pat. No. 3,860,733 is incorporated herein by reference in its entirety. Another description of the preparation of ethylcellulose microcapsules by the liquid-liquid phase separation of ethylcellulose in cyclohexane is given in U.S. Pat. No. 4,411,933, which patent disclosure is also incorporated herein by reference in its entirety.

A microencapsulation polymer is used to encapsulate the antibiotic in a polymeric coating matrix prepared by solvent coacervation. Microencapsulation polymers suitable for use in the present invention include ethylcellulose, cellulose acetate phthalate, hydroxypropyl methylcellulose phthalate, anionic methacrylic acid-acrylate copolymers, neutral methacrylic acid esters and polyvinyl acetate. Preferably, the microencapsulation polymer is cellulosic and, in particular, ethylcellulose. Ethylcellulose used in the microencapsulation typically has an ethoxy content of about 45 to 50% and a viscosity in the range of 14 to 100 cps at 25° C. The amount of ethylcellulose employed can vary but for taste masking purposes, the ethylcellulose typically comprises about 10% to 40% by weight of the coated granules. One useful ethylcellulose is Ethylcellulose, NF manufactured by Dow Chemical Company having a 49.4% ethoxy content and a 103 cps viscosity at 25° C.

Any pharmaceutically acceptable organic solvent in which the active ingredient is not soluble but the polymer is soluble is suitable for microencapsulation, though the solvent of choice is cyclohexane. A coacervation inducer such as polyethylene, polyisobutylene, and the like, may be dissolved in the coacervation solution in which Linezolid is suspended. The polymers suitable for use as the coacervation inducer can have a molecular weight of between 5,000 and 10,000 and can be any of the commercial types customarily used for encapsulating purposes. One example of a useful polyethylene is Epolene C-10 manufactured by Eastman Kodak Company. The concentration of ethylcellulose and polyethylene and the wall thickness should be optimized for a particular formulation. The polyethylene is typically used in an amount of about 0.5 to 2% by volume.

After application of the ethylcellulose, a drying step should preferably be carried out for such a time period and at such temperatures so as to reduce residual solvent level below that recommended for human consumption.

These microencapsulated crystals are provided with an enteric polymer coat. Enteric polymers suitable for functional coating include methacrylic ester (Eudragit L and S) copolymer, cellulose acetate phthalate and hydroxypropyl-methyl cellulose phthalate. Particularly preferred enteric polymers are methacrylic acid-methylmethacrylate copolymers and methacrylic acid-ethylmethacrylate copolymers. These polymers can be plasticized using conventional plasticizers in an amount of about 5 to 30% based on the weight of the entire polymer. Representative examples of plasticizers are polyethylene glycol, dibutyl sebacate, diethyl phthalate, phthalic acid derivatives and citric acid esters (acetyl tributyl citrate, triethyl citrate). Both aqueous and solvent based functional coating materials can be used.

The coating materials are applied in an amount of about 30 to 60 wt % based on the total weight of the coated particles. The microencapsulation polymer typically represents 5 to 30 wt %, preferably 8 to 15 wt %, the enteric polymer typically is 20 to 50 wt %, preferably 35 to 45 wt %, and the optional seal coat is present at up to 3%, preferably up to 2%, of the total weight of the coated particles.

The ethylcellulose microencapsulation and the enteric coating processes may optionally be replaced by a single microencapsulation process using the solution of an enteric cellulosic polymer such as cellulose acetate phthalate.

The material of choice for the seal coat is plasticized pharmaceutical grade shellac. Other seal coat materials such as Colorcon Opadry, a plasticized hydroxypropylmethylcellulose (HPMC) formulation, can be used for the same purpose.

Both seal and enteric coatings can be formed by spraying solutions in organic solvents or suspensions in purified water. The seal coat may also be applied as an outer coat. The polymeric coatings may contain certain pigments and opacifiers to promote compliance, product differentiation or purely for aesthetic reasons.

The mean particle size of the microcapsules will be in the range of about 30 to 1000 microns, most preferably in the range of about 100 to 500 microns.

The different lots of the taste-masked granules have been found to release less than 2% at pH 4.0 (which is an approximate pH for saliva) in an hour but not less than 70% in an hour at pHs of the upper intestinal tract when dissolution tested using USP Apparatus 2 (900 mL of pH 4.0 or pH 6.8 buffer, Paddles @ 50 rpm and 100 rpm, respectively).

Various types of formulations may be prepared using the taste masked Linezolid microcapsules disclosed in this invention, including liquid suspensions or dispersions, capsules filled with free-flowing particulate material, effervescent tablet, fast disintegrating tablet, and chewable tablet formulations. These solid or liquid formulations may contain about 10 weight % to 95 weight % microcapsules. Actual methods of preparing such dosage forms are well known to those skilled in this art. For these formulations, conventional carriers, sweeteners, flavoring/coloring additives and tableting aids will be employed, which include, but are not limited to, ingredients such as binders, disintegrants, wetting agents, diluents and lubricating agents. Binders include, but are not limited to, Klucel ® LF (hydroxypropylcellulose) and Avicel ® (microcrystalline cellulose). Disintegrants include, but are not limited to, cornstarch, lactose, mannitol, sucrose, Avicel ® (microcrystalline cellulose), Primogel ® (sodium carboxymethyl starch, Emcompress ® (dibasic calcium phosphate dihydrate), Crospovidone ® (cross linked polyvinyl pyrrolidone), and tricalcium phosphate. Wetting agents include, but are not limited to, sodium lauryl sulfate. Lubricating agents include, but are not limited to stearates (e.g. magnesium, calcium, and sodium), stearic acid, Sterotex ®, talc, waxes, and Stearowet ®. Components will be incorporated in formulations, which promote effervescence, i.e., release of gas (carbon dioxide) upon contact with water; these components include a combination of a carbonate salt, such as sodium bicarbonate, and an organic acid such as citric acid.

In addition to the dosage forms listed earlier, the taste masked microcapsules, due to their free flowing characteristics, may be used in the development of sustained/modified release tablet/capsule formulations. Additional objects, advantages and novel features of the invention will become apparent to those skilled in the art upon examination of the examples provided, or upon practicing the invention.

EXAMPLES

Example 1

Linezolid crystals with a median particle size of 20 microns are well dispersed in 5 gallon microencapsulation tank filled with cyclohexane containing 3% ethylcellulose (Ethocel Standard 100 Premium, Dow Chemical Company) with a viscosity range of 90–110 cps. The temperature of the suspension is raised to 80° C. with agitation to dissolve ethylcellulose. The system is cooled gradually to 45° C. over one hour and then rapidly to room temperature to induce coacervation, i.e., to wrap Linezolid particles with a uniform film at 30% weight gain. These microcapsules are coated in a fluid bed coating unit, Versa Glatt, with a suspension of Eudragit L30D for 30% weight gain, with triethyl citrate as the plasticizer. The taste masked granules thus obtained are found to release in an hour 2.8% and 76% when tested at pH 4.0 and 6.8, respectively using USP Apparatus 2 (900 mL of pH 4.0 or pH 6.8 buffer, Paddles @50 rpm and 100 rpm, respectively).

Example 2

The composition of the microencapsulation tank of Example 1 is changed to obtain an ethylcellulose coating of 20% weight gain. These microcapsules are first coated using Glatt GPCG 5 fluid bed coater with a seal coat of 3% shellac and further coated with a suspension of Eudragit L30D for 30% weight gain, with acetyl tributyl citrate as the plasticizer. The taste masked granules have been observed to release in an hour 1.1% at pH 4.0 and 76% at pH 6.8. The microcapsules are blended with additional suspension aids including flavor and sweetener and filled into unit dose containers for oral administration as an aqueous suspension.

Example 3

The composition of the microencapsulation tank of Example 1 is changed to obtain an ethylcellulose coating of 20% weight gain. These microcapsules are coated for 40% weight gain with a suspension of the 4:1 blend of Eudragit L30D and ethylcellulose (Aquacoat ECD-30 from FMC), with triethyl citrate and dibutyl sebacate, respectively, as the plasticizer. The taste masked granules have been observed to release in an hour 1.4% at pH 4.0 and 95% at pH 6.8.

Example 4

An effervescent tablet formulation has been developed using the taste masked Linezolid granules manufactured in Example 2. Table 1 lists the ingredients used. Thoroughly distribute light mineral oil (6) on 400 g sodium bicarbonate. Blend flavor and color with 100 g sodium bicarbonate. Mix thoroughly Linezolid granules, citric acid, and the above blends in a blender and compress into beveled-edge tablets, each tablet (80 mg dose) weighing 552 mg.

Example 5

A fast disintegrating tablet formulation has been developed using the taste masked Linezolid granules manufactured in Example 2. Table 1 lists the ingredients used. Thoroughly distribute flavor, sweetener, BMI-60, and color on Linezolid granules. Blend spray dried mannitol, xylitol and the above blend in a blender and compress into beveled-edge tablets, each tablet (100 mg dose) weighing 690 mg. These tablets are suitable for oral administration without water for patients who find it difficult to swallow regular tablets, and have been observed to disintegrate rapidly in the mouth (generally in 30 seconds or less).

Example 6

A chewable tablet formulation has been developed using the taste masked Linezolid granules manufactured in Example 3. Table 1 lists the ingredients used. Thoroughly distribute flavor and color on Linezolid granules blend spray dried mannitol, sorbitol, Avicelo CE-15 (a patented excipient from FMC, a combination of microcrystalline cellulose and gaur gum) and the above blend in a blender for 10 min, and further blend for an additional 5 min after adding stearic acid as the lubricant. The compressed tablets (20 mg dose) weighing 250 mg are suitable for oral administration, especially for children.

Example 7

A controlled release tablet formulation has been developed using the free flowing coated Linezolid granules of Example 2. 208.3 g of Linezolid granules are blended with 27.0 g of HPMC K4M, 18.0 g of Klucel EF (HPC), 42.0 g hydrous lactose and 4.7 g stearic acid and compressed into 100 mg controlled release Linezolid tablets (tablet weight: 300 mg) which would provide an extended release profile when dissolution tested in an alkaline buffer (USP apparatus 2, Paddle @ 50 rpm in 900 mL buffer at pH 6.8).

TABLE 1

Formulation Details

| Ingredients (g) | Effervescent Tablet (Ex. 4) | Fast-disintegrating Tablet (Ex. 5) | Chewable Tablet (Ex. 6) |
| --- | --- | --- | --- |
| Linezolid granules | 320 | 320 | 320 |
| Sodium bicarbonate (granular) | 450 | | |
| Citric acid, anhydrous (granular) | 350 | | |
| Mannitol, spray-dried | | 400 | 200 |
| Xylitol | | 380 | |
| Sorbitol | | | 520 |
| Flavor (spray-dried) | 50 | 20 | 40 |
| Color | 10 | 10 | |
| Avicel ® CE-15 | | | 100 |
| Aspartame | | 10 | |
| BMI-60 | | 20 | |
| Disintegrant | | 30 | |
| Lubricant | 20 | 10 | 20 |

Having described the invention in detail, it will be apparent that modifications and variations are possible without departing from the scope of the invention defined in the appended claims.

What is claimed is:

1. A taste masked microcapsule composition for taste masking an orally effective oxazolidinone antibiotic, comprising the microcapsules of the drug in a polymeric coating matrix prepared by solvent coacervation of a microencapsulation polymer and provided with an optional seal coat and a coating of a plasticized enteric polymer, wherein the coating materials are applied in the range of approximately 30 wt. % to 60 wt.% of the composition.

2. The composition of claim 1, wherein the microcapsules by themselves or in a pharmaceutically acceptable dosage form, release not more than 5% at pHs of the saliva but rapidly release at least 70% within approximately an hour at pHs of the upper intestinal tract.

3. The composition of claim 2 wherein the microcapsules by themselves or in a pharmaceutically acceptable dosage form, release not more than 3% at pHs of the saliva.

4. The composition of claim 1, wherein the microencapsulation polymer comprises ethylcellulose, the enteric polymer is selected from the group consisting of cellulose acetate phthalate, hydroxypropyl methylcellulose phthalate and methylmethacrylate copolymers, and the optional seal coating material is shellac or a plasticized hydroxypropyl methylcellulose formulation.

5. The composition of claim 4, wherein the microencapsulation polymer is ethylcellulose, the enteric polymer is an enteric methylmethacrylate copolymer and the optional seal coating material is shellac.

6. The composition of claim 1, wherein the microencapsulation polymer represents approximately 5 to 30 wt. %, the enteric polymer 20 to 50 wt. %, and the optional seal coat up to 3 wt. % based on the total weight of the microcapsule composition.

7. The composition of claim 6, wherein the microencapsulation polymer represents 8 to 15 wt. %, the enteric polymer 35 to 45 wt. %, and the optional seal coat up to 2 wt. % of the microcapsule composition.

8. The composition of claim 7 wherein the microencapsulation polymer is ethylcellulose, the enteric polymer is methacrylic acid-methylmethacrylate copolymer or methacrylic acid-ethylacrylate copolymer, and the optional seal coat is shellac.

9. The composition of claim 1, wherein the drug is Linezolid.

10. A pharmaceutical formulation for administering an oxazolidine antibiotic comprising the taste-masked composition of claim 1 and a pharmaceutically acceptable carrier.

11. The pharmaceutical formulation of claim 10, wherein the formulation is an aqueous suspension.

12. The pharmaceutical formulation of claim 10 in the form of a free-flowing particulate material filled in a capsule.

13. The pharmaceutical formulation of claim 10 in the form of a compressed tablet.

14. The pharmaceutical formulation of claim 13, which further comprises a combination of a carbonate salt and an organic acid representing on the order of approximately 5 to 50 wt. % of the formulation by weight.

15. The pharmaceutical formulation of claim 14 wherein said carbonate salt is sodium bicarbonate and said organic acid is citric acid.

16. A pharmaceutical formulation of claim 10 in the form of a fast-disintegrating tablet.

17. A pharmaceutical formulation of claim 10 in the form of a chewable tablet.

18. A pharmaceutical formulation of claim 10 in the form of a controlled release tablet.

19. A method for masking the bitter taste of an orally effective oxazolidinone antibiotic comprising:

a) microencapsulating particles of the antibiotic in a polymer by coacervation in cyclohexane b) applying a seal coat and c) applying a membrane coating of an enteric polymer.

20. The method of claim 19 wherein the antibiotic is Linezolid.

21. The method of claim 19 wherein the method yields a coated particle which is characterized by not more than 5% release at the pH of the saliva but rapid release at the pH of the upper intestinal tract.

* * * * *